United States Patent
Maurer et al.

(10) Patent No.: US 7,581,444 B2
(45) Date of Patent: Sep. 1, 2009

(54) METHOD AND CIRCUIT ARRANGEMENT FOR DISTURBANCE-FREE EXAMINATION OF OBJECTS BY MEANS OF ULTRASONIC WAVES

(75) Inventors: Albrecht Maurer, Seligenstadt (DE); Michael Strauss, Moembris (DE); Walter De Odorico, Kelkheim (DE); Roman Koch, Blankenbach (DE)

(73) Assignee: GE Inspection Technologies GmbH, Alzenau (DE)

( * ) Notice: Subject to any disclaimer, the term of this patent is extended or adjusted under 35 U.S.C. 154(b) by 504 days.

(21) Appl. No.: 10/564,737

(22) PCT Filed: Jul. 19, 2004

(86) PCT No.: PCT/EP2004/008048
§ 371 (c)(1), (2), (4) Date: Jan. 19, 2006

(87) PCT Pub. No.: WO2005/012941
PCT Pub. Date: Feb. 10, 2005

(65) Prior Publication Data
US 2006/0195273 A1    Aug. 31, 2006

(30) Foreign Application Priority Data
Jul. 29, 2003    (DE) .................... 103 34 902

(51) Int. Cl.
*G01N 29/024*    (2006.01)
(52) U.S. Cl. .................. 73/597; 73/598; 73/599; 73/602; 73/628
(58) Field of Classification Search .......... 73/600, 73/602, 622, 624, 625, 628, 597, 598, 599, 73/626, 627; 702/39
See application file for complete search history.

(56) References Cited

U.S. PATENT DOCUMENTS 4,537,073 A * 8/1985 Ooshiro et al. ............... 73/602

(Continued)

FOREIGN PATENT DOCUMENTS

DE    3236017    3/1984

(Continued)

OTHER PUBLICATIONS

Elbern, Synthetic Aperture Focusing Technique for Image Restauration, vol. 5, No. 08, pp. 2-6, 2000.

(Continued)

*Primary Examiner*—J.M. Saint Surin
(74) *Attorney, Agent, or Firm*—Dennison, Schultz & MacDonald (57) ABSTRACT

A method and circuit arrangement for processing signals which are produced during disturbance-free examination of objects such as pipes or sheet metal, by reflecting ultrasonic waves at defective spots on the structure of the object. According to the method, a complete wave front is emitted on at least one section of the object which is to be examined by means of a plurality of independent transmitting elements, a wave reflected by the structure of the object is received by means of a plurality of receiving elements which are independent of each other, the signals received by the receiving elements are digitalized, and the digitalized signals are stored in a storage element according to amplitude and propagation time. In order to detect defective points on the structure of the object in a faster manner with improved signal/noise ratio, the defective points are detected by a phase-locked addition of the stored amplitude values of the propagation time.

22 Claims, 8 Drawing Sheets

U.S. PATENT DOCUMENTS

| | | | | |
|---|---|---|---|---|
| 4,766,554 A * | 8/1988 | Sarr et al. | ...................... | 702/39 |
| 5,019,786 A * | 5/1991 | Fairley et al. | ............ | 324/76.77 |
| 5,060,205 A * | 10/1991 | Phelan | ........................ | 367/98 |
| 5,388,182 A * | 2/1995 | Benedetto et al. | ........... | 704/205 |
| 5,804,731 A * | 9/1998 | Jaeggi | ........................ | 73/636 |
| 6,023,660 A * | 2/2000 | Dory | ........................ | 702/39 |
| 6,789,427 B2 * | 9/2004 | Batzinger et al. | ............. | 73/614 |
| 6,843,313 B2 * | 1/2005 | Hult | ........................ | 166/78.1 |
| 7,231,304 B2 * | 6/2007 | Mitchell | ..................... | 702/35 |
| 7,293,461 B1 * | 11/2007 | Girndt | ........................ | 73/622 |
| 2003/0136195 A1 * | 7/2003 | Krieg et al. | .................. | 73/628 |
| 2008/0178678 A1 * | 7/2008 | Girndt | ........................ | 73/622 |

FOREIGN PATENT DOCUMENTS

| | | |
|---|---|---|
| WO | 92/00584 | 1/1992 |
| WO | 00/68931 | 11/2002 |

OTHER PUBLICATIONS

Mahaut, An Adaptive System for Advanced NDT Applications Using Phased Arrays, Ultrasonics, IPC Sci. Etc., pp. 128-131, 1998.

Mahaut, Development of Phased Array Techniques to Improve . . . Geometry, Ultrasonics, IPC Sci. Etc., pp. 165-169, 2002.

Cassereau, The Phased Array Technology etc., IEE Inter. Conference, pp. 461-464, 2000.

Roy, Control of the Ultrasonic Beam . . . and Application, Ultrasonics, IPC Sci. Etc., pp. 243-246, 2002.

\* cited by examiner

Fig.9 delayed shot for transmitting and receiving to be parallel to surface contour

Fig. 11

B-scan planar parallel shot to calibrate surface contour

Fig. 10

METHOD AND CIRCUIT ARRANGEMENT FOR DISTURBANCE-FREE EXAMINATION OF OBJECTS BY MEANS OF ULTRASONIC WAVES

This application is a filing under 35 USC 371 of PCT/EP2004/008048 filed Jul. 19, 2004.

BACKGROUND OF THE INVENTION

The invention relates to a method for processing signals and to a circuit arrangement.

A method for processing signals which correspond to reflected waves which are transmitted or interrupted by a structure in order to be able to gather information and analyze the structure of this material is described in EP 0 825 453 B1. With the method described, the fact that every point of an object to be examined leads to a reflected wave which is then stored at positions of the storage unit which are distributed in the form of parabolic curves, the characteristics of which depend on the distance of the point relative to the probe and on the radiation pattern of each element. In the known method, a probe is used which is configured linearly and composed of a plurality of transmitter/receiver elements of small dimensions. The same probe is then used for transmission and reception. First, a wave front is transmitted into the object to be examined and those waves which are reflected by the structure are received.

The information which is emitted by the sensor elements is then digitalized and stored and, more particularly, is stored in a storage element which has a line for each sensor element.

Subsequently, the structure of the object is reconstructed and/or analyzed with reference to the information that was stored in the storage elements. For each point of the object the position of the storage element is computed which contains the signals which are located by the sensor elements and correspond to the waves reflected or transmitted from this point. This position is computed with aid of an addressing rule whose parameters depend on the position of this point in relation to the sensor elements. Furthermore, the lines of the field storage are read for each point at the respective positions which were previously computed for this point, a mathematical operation being used for the values read for this point in order to obtain a result which is representative for the range of the wave. For the computation, all cells of the storage field are read in parallel for this point at the positions which are designated for this point in the respective allocated addressed storage units.

Since the computation of each reading principle for reading out the storage would take too long to effect in real time, this computation is done in advance and the results stored in specific "address storage units" which are allocated to each line of the "field storage unit".

Hence, it follows that the described method is only suitable for identifying specific, i.e. previously defined structures. After performing the mathematical operation, the contents of the field storage unit are stored in image storage unit, location and propagation time information being taken into consideration. In the method, computed B images are evaluated, as is common, for example, in medical diagnostics. However, for automatic material examination, B images should not be referred to since long evaluation times are required for the evaluation.

Furthermore, it should be noted that there are limits in defect detection with vertical acoustic irradiation since only one defective position can be detected. Furthermore, uncertainties occur in the defect evaluation, since fixed geometric relations between the probe and the test piece are a prerequisite, since location information is required for the defect determination. Therefore, the known method is very sensitive to conventional misalignments of the probe.

SUMMARY OF THE INVENTION

Based on this, the object of the present invention is to further develop a method and a circuit arrangement of the known type in such a way that defect locations of the structure of the object can be detected at high speed and with an improved signal/noise ratio. Furthermore, the method should be insensitive to possible misalignments of the probe.

It is thereby provided that a defect location is determined by a phase-locked addition of the stored amplitude values received at equal propagation times. Use is hereby made of the fact that, when an object is radiated by means of a probe configured as a Phase Array Transducer, i.e. when emitting a complete wave front, echoes are received in each of the receiver elements of the probe switched simultaneously to receive, the amplitude values of the received echoes being received at the same propagation times. This offers the possibility of adding the amplitude values of the received signals along a propagation time, with the advantage that the amplitude peaks identifying the defect location in the structure are amplified and that the additional signals received by the individual receiver elements almost cancel one another.

Consequently, the method according to the invention is distinguished, on the one hand, by a very high speed of defect identification, since the sequential method common in the prior art is avoided due to the emission of a complete wave front and, on the other hand, by an improved signal/noise ratio being obtained in comparison to the prior art. The method is also robust against e.g. a misalignment of the probe, since location information is not involved in the method.

To identify defect locations on an outer surface of the object (outer field), in particular during the non-destructive examination of pipes by means of ultrasound, point-wave signals which proceed from reflections at outer defects of the object are evaluated. An addition of the amplitude values stored in the storage unit does thereby not take place along one and the same propagation time, but in a direction which extends at a right angle, or essentially at a right angle, to the interference patterns of the received amplitude values of the point-waves of the outer defects AF.

Due to the phase-locked addition of the amplitude values along a propagation time, defect locations can generally be identified, whereby, however, information about whether or not it is an outer defect or an inner defect cannot be derived from the sum signal. As previously stated, outer defects can be identified by adding amplitude values at a right angle or essentially at a right angle to interference patterns of the point-waves emanating from the outer defect. Finally, a comparison of the signal detected during the phase-locked addition of stored amplitude values along a propagation time with the signal detected during the addition of the amplitude values of the interference patterns takes place due to a coincidence circuit, in which an outer defect is present when both signals indicate a defect location.

To set a beam angle α adapted to the measuring conditions, e.g. type of defect (longitudinal defect, inclined defect), property of the material and the shape of the object to be examined, the individual transmitter elements of the Phased Array Transducers can be controlled in a time-delayed manner (phasing). When examining e.g. a pipe, an ultrasonic irradiation can take place in dependence on a defect location (inclined defect, longitudinal defect), optionally in the longitudinal direction or in the peripheral direction.

Furthermore, it is provided that, to determine the location of the defect, a propagation time dependent amplitude correction of the sum signal determined during the addition can be carried out, the received sum signal being compared with a reference value.

To further reduce the data, it is provided that the received signals are filtered immediately after the digitalization, preferably by means of a wavelet filter.

The object is solved by a circuit arrangement in which a summer is provided for the phase-locked addition of the amplitude values stored in the storage module.

Furthermore, the invention relates to a method for the non-destructive examination of a contour, such as an edge, bend or curvature of an object.

According to the prior art, contours of the aforementioned type in the form of edges are examined by ultrasound with an essentially planar wave front. An interference pattern corresponding essentially to the contour of the object to be examined is thereby received, but the interference pattern is unsuitable for evaluating defect locations in the structure of the object.

Based on this, the object of the invention is to provide a method for the non-destructive examination of a contour of an object by means of ultrasonic waves which enables an improved identification of defect points in the structure of the object in the area of the contour.

To achieve the object, it is proposed that the contour of a surface of the section of the object to be examined is detected and stored, that the independent transmitter elements are controlled in a time-delayed manner in such a way that the emanating wave front extends parallel or approximately parallel to the surface contour and that the waves reflected by the object are received in a time-delayed manner and produce an essentially planar interference pattern.

In a preferred procedure, it is provided that the contour of the object is identified by transmission a wave front which is planar relative to a transmission plane to the contour to be examined, that the waves reflected by the contour of the object are received and digitalized by means of the plurality of receiver elements that are independent of one another and the digitalized signals are stored in the storage element at least according to their propagation time and that the contour of the object is computed from the defined distance A of the probe to the object and the different propagation times of the received signals.

The method is distinguished by a time-delayed actuation of the independent transmitter elements which transmit a wave front in such a way that it extends parallel or essentially parallel to a surface of the structure of the object to be examined.

When the wave reflected by the contour of the object is received, a time-delayed reception by means of the controllable receiver elements also occurs, as a result of which signals are received which generate an interference pattern extending parallel or essentially parallel to the surface of the contour of the object. Defect locations of the structure of the object can then be easily identified in this interference pattern.

Due to fluctuations in production, irregularities can occur in the contour of the object to be examined, so that, according to a further preferred procedure, it is provided that the contour of the object is preferably identified on-line, i.e. during a measurement process. For this purpose, it is provided that a planar wave front is transmitted onto the contour to be examined, that the waves reflected by the contour of the object are received and digitalized by means of the plurality of receiver elements which independent of one another and the digitalized signals are stored at least according to propagation time in a storage element and that the contour of the object is computed from the defined distance of the probe to the object and the varying propagation times of the received signals.

By the on-line resetting or adjustment to the changing contour of the object, an always uniform evaluation of defect locations is possible.

The readjustment is made possible by comparing the received interference pattern extending parallel or essentially parallel to the contour of the surface of the object with a desired pattern, a wave front which is parallel or essentially parallel relative to the plane of the transmitter element being emitted when the received interference pattern deviates from the desired pattern in order to compute the actual contour of the object to be examined from the reflected waves.

BRIEF DESCRIPTION OF THE DRAWINGS

Further details, advantages and features of the invention can be found not only in the claims, the features found therein—alone and/or in combination—but also in the following description of a preferred embodiment that can be found in the drawings, in which:

DESCRIPTION OF THE PREFERRED EMBODIMENTS

Figure 1:
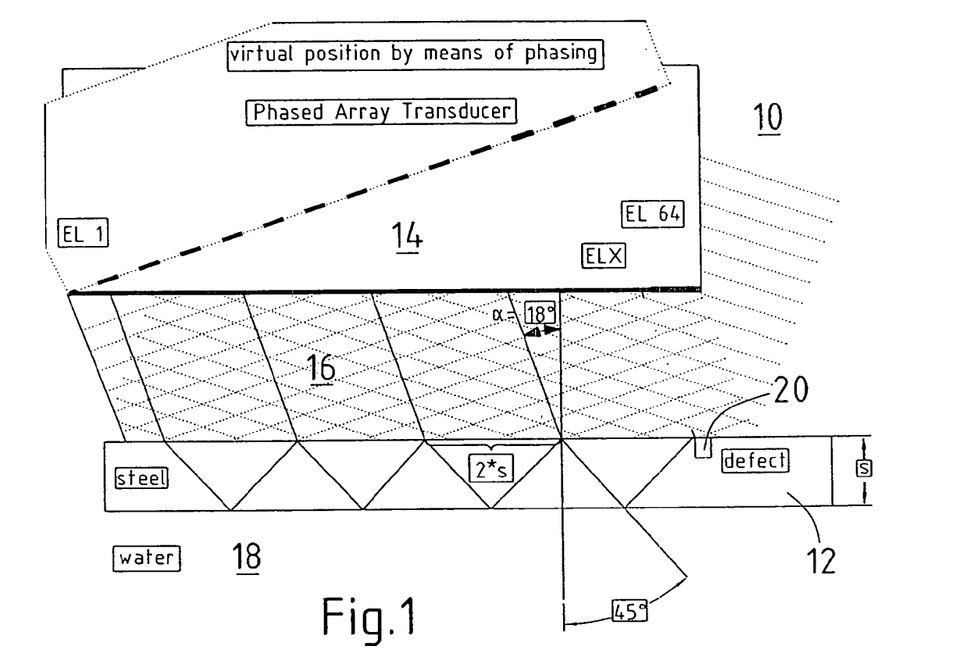
FIG. 1 shows a schematic representation of a wave front emanating from a probe (Phase Array Transducer) through a medium such as water onto an object to be examined, e.g. a steel plate.

FIG. 1 shows, in a purely diagrammatic manner, an arrangement 10 for the non-destructive examination of an object 12 which is shown as a steel plate in the illustrated embodiment, by means of an ultrasonic wave front 16 emanating from a probe 14, the ultrasonic wave front being coupled into the object 12 through a liquid medium 18 such as water. Defect locations 20 in the structure of the object 12 are to be detected by the examination.

The probe 14 comprises a plurality of transmitter/receiver elements EL1 to ELN which are each preferably switched simultaneously or phase-displaced as transmitter elements and preferably simultaneously as receiver elements.

Figure 2:
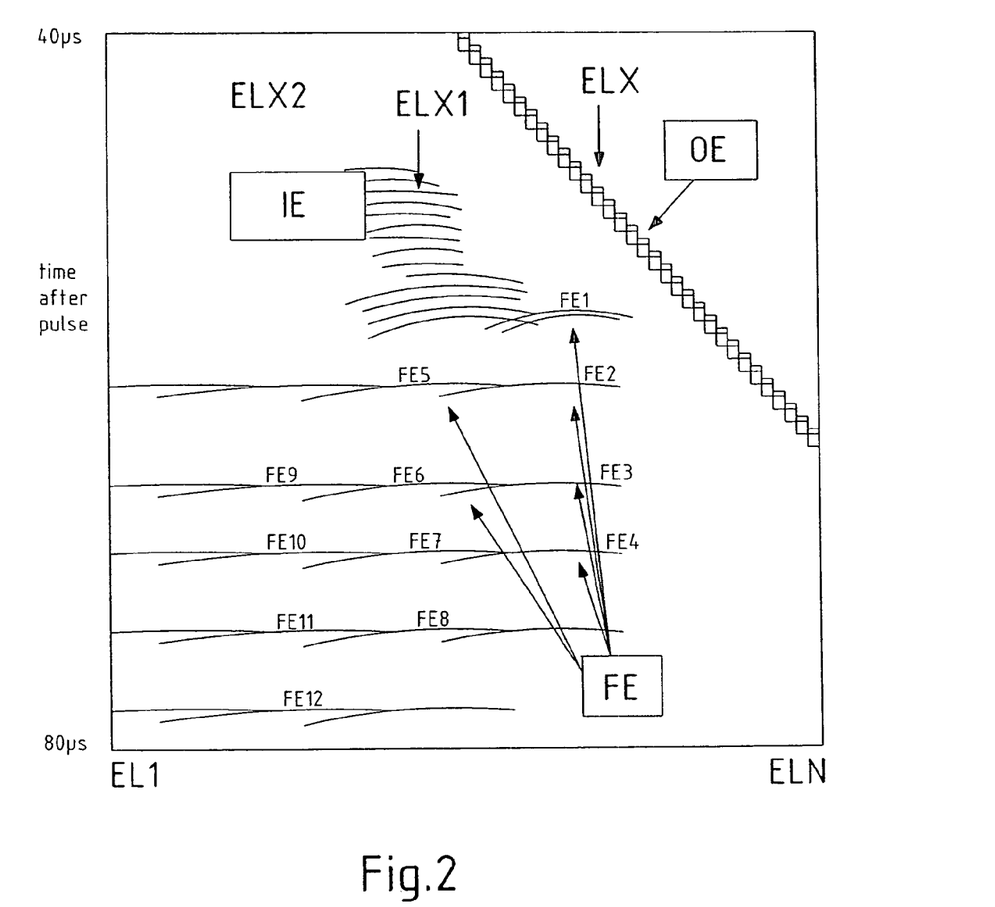
FIG. 2 shows a representation of amplitude values of the amplitudes received from the individual receiver elements EL1-ELN of a probe with varying propagation times (typical B-scan)

With reference to a grey-scale image, FIG. 2 shows a conventional B-scan of an outer defect location of a planar object which was taken with a Phased Array Transducer at a beam angle of α=18°. The wave front transmitted onto the object 12 was generated by simultaneous switching on of all transmitter elements.

The individual receiver elements EL1-ELN are plotted over the horizontal axis, the signals received from the individual receiver elements being shown according to their propagation time which is plotted over a vertical axis, in succession in the vertical direction.

The intensity of the illustrated signals is defined by their brightness. It can be seen in the B-scan of FIG. 2 that different structures of the object generate different signal patterns. Thus, the surface of the object 12 generates surface echoes OE which are shown as diagonally extending, continuous lines in FIG. 2. The defect echoes FE1-FE12 allocated to the individual receiver elements EL1-ELN are shown as horizontal lines. Thus, for example, the defect echoes FE1 to FE4 of a receiver element ELX and the defect echoes FE5 to FE8 or the defect echoes FE9 to FE 12 of additional receiver elements ELX1, ELX2, respectively, are shown. In the upper left area of the B-scan, interference echoes IE can be identified which are produced due to interferences between wave fronts of the individual transmitter elements of the Phase Array Transducer.

Furthermore, the B-scan shown in FIG. 2 shows that defect echoes of several receiver elements, e.g. the defect echoes FE1, FE5 and FE3, FE6, FE9 as well as FE4, FE7 and FE10, are each received at equal propagation times. The same propagation times of, for example, the defect echoes FE2 and FE5 as well as FE3 and FE6 are to be described with reference to FIG. 3.

Figure 3:
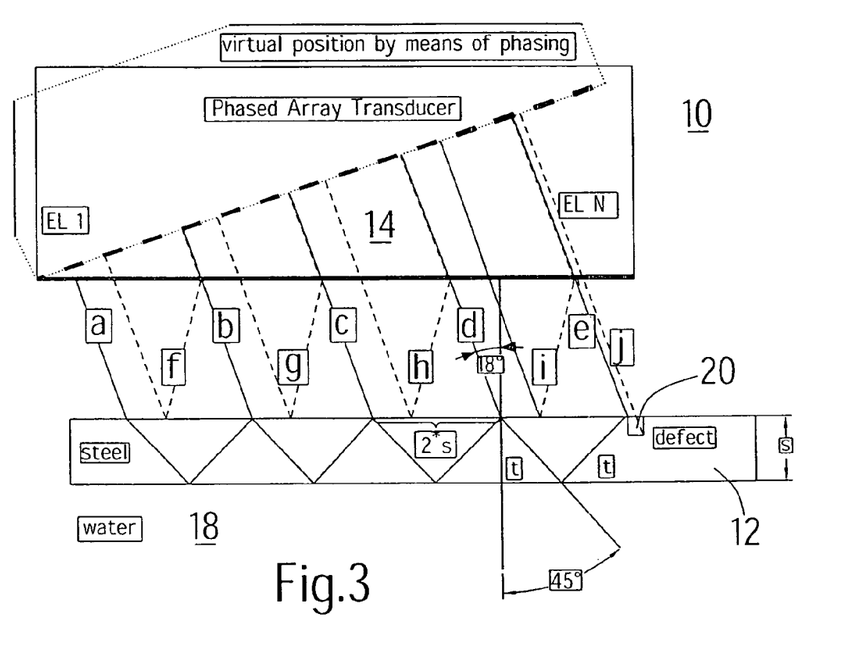
FIG. 3 shows a representation of selected ray paths of the ultrasonic wave front according to FIG. 1.

The structure according to FIG. 1 is shown in FIG. 3, signal paths a to i being shown purely diagrammatically. The thickness of the steel plate is designated by s and the ray path within the object 12 by t.

It appears that the propagation time of the defect echo FE2 from the sections d+2t+e and the propagation time of the defect echo FE5 from the sections or propagation times e+2t+d each comprise an identical propagation time. The propagation times of the defect echo FE3 and defect echo FE6 are also identical, it being noted that they are received in different receiver elements.

Figure 4:
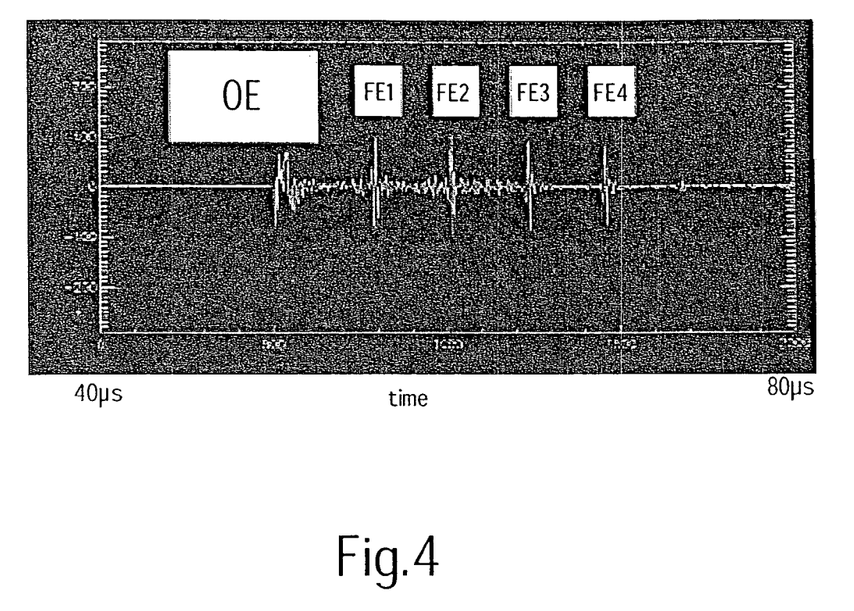
FIG. 4 shows a representation of the amplitude curve over the propagation time of an individual receiver element ELX according to FIG. 2.

The signals received from a receiver element ELX can also be shown in their amplitude over time. A corresponding illustration (A-scan) is shown in FIG. 4. In this case, the individual echoes OE, FE1 to FE4 are shown as amplitude swings at different propagation times. According to the method of the invention, the amplitude values of the signals received at the same propagation times, e.g. FE2 and FE5, FE3, FE6, FE9, or FE4, FE7 and FE10, are added along their propagation time, the signal shown in FIG. 5 being obtained over the time which very clearly represents information about the field position 20 in the object 12 by an amplitude increase in the range of an order of magnitude.

Since the defect echoes received from various elements ELX, ELX1 or ELX2 have the same propagation time, the amplitude values are added, so that the sum signal increases. Since the noise signals contained in the A-scan of FIG. 4 cancel one another stochastically, the signal/noise ratio is improved.

Figure 6:
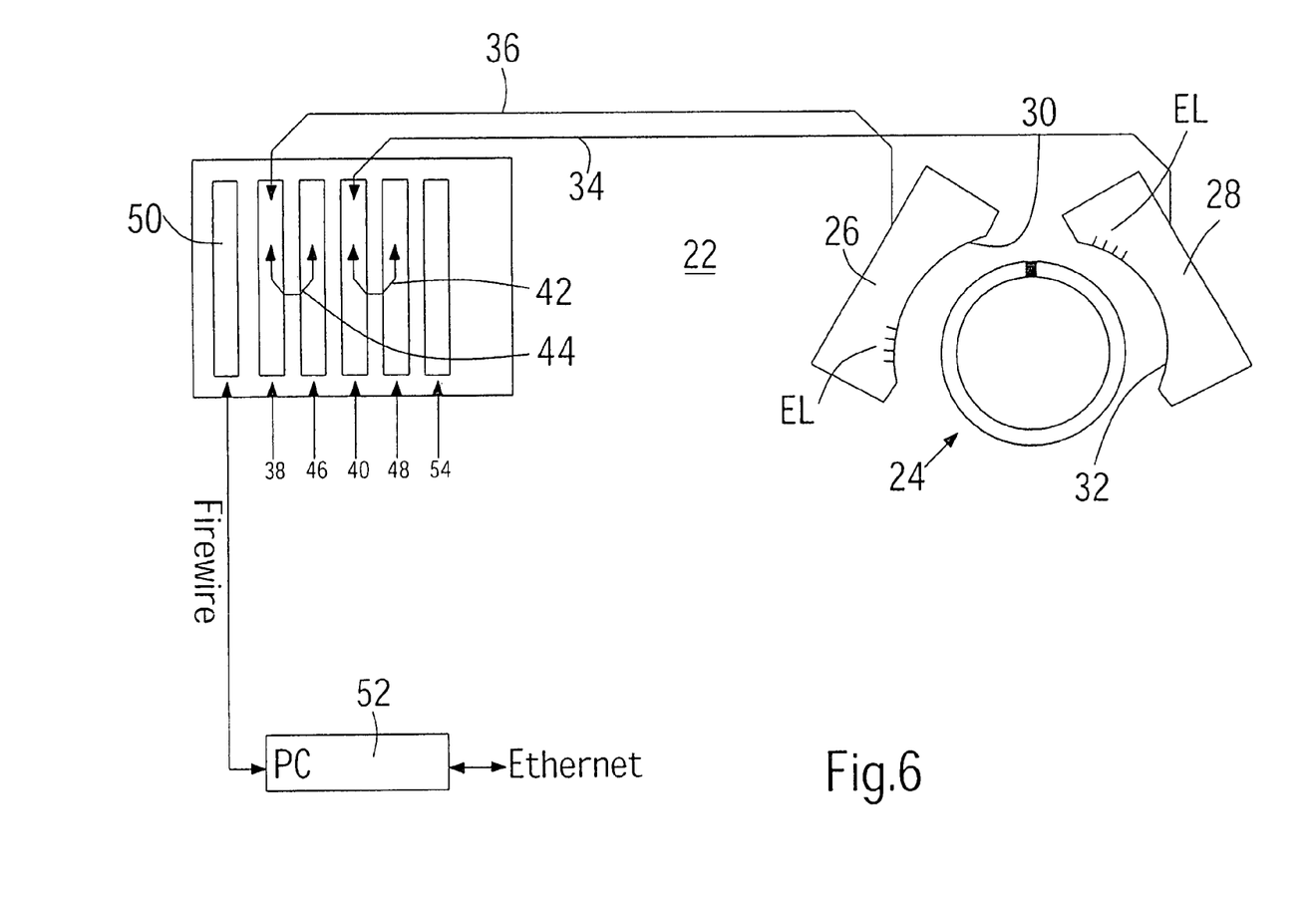
FIG. 6 shows a test assembly in principle for the non-destructive examination of a pipe.

FIG. 6 shows a test assembly 22 for the non-destructive examination of a pipe wall 24 by means of probes 26, 28 which are arranged along the periphery of the pipe and have curved surfaces 30, 32 adapted to the surface of the pipe 24, to which the transmitter/receiver elements EL1 to ELN, N being e.g. 128, of each element transmitter/receiver element EL1-ELN can be switched both as a transmitter and as a receiver (sic). The spatial extent of an element is adapted to the ultrasonic frequency f used, which is in the range of 0.2 MHz≦f≦20 MHz, preferably f=6 MHz.

The probes 26, 28, which are also designated as Phased Array Transducers, are each connected via data lines 34, 36 with a first signal processing unit 38, 40 which controls the transmitter/receiver element EL of the probes 26, 28 and amplifies and digitalizes the received signals. The signal processing units 38, 40 are each connected to a signal evaluation unit 46, 48 via a data connection 42, 44, which can e.g. be configured as FSL (Fast Serial Link). Furthermore, the circuit arrangement comprises an interface 50 for connection to an external personal computer 52 and a microprocessor unit 54 for processing and evaluating (sorting, marking) the information from the units 46 and 48.

Figure 7:
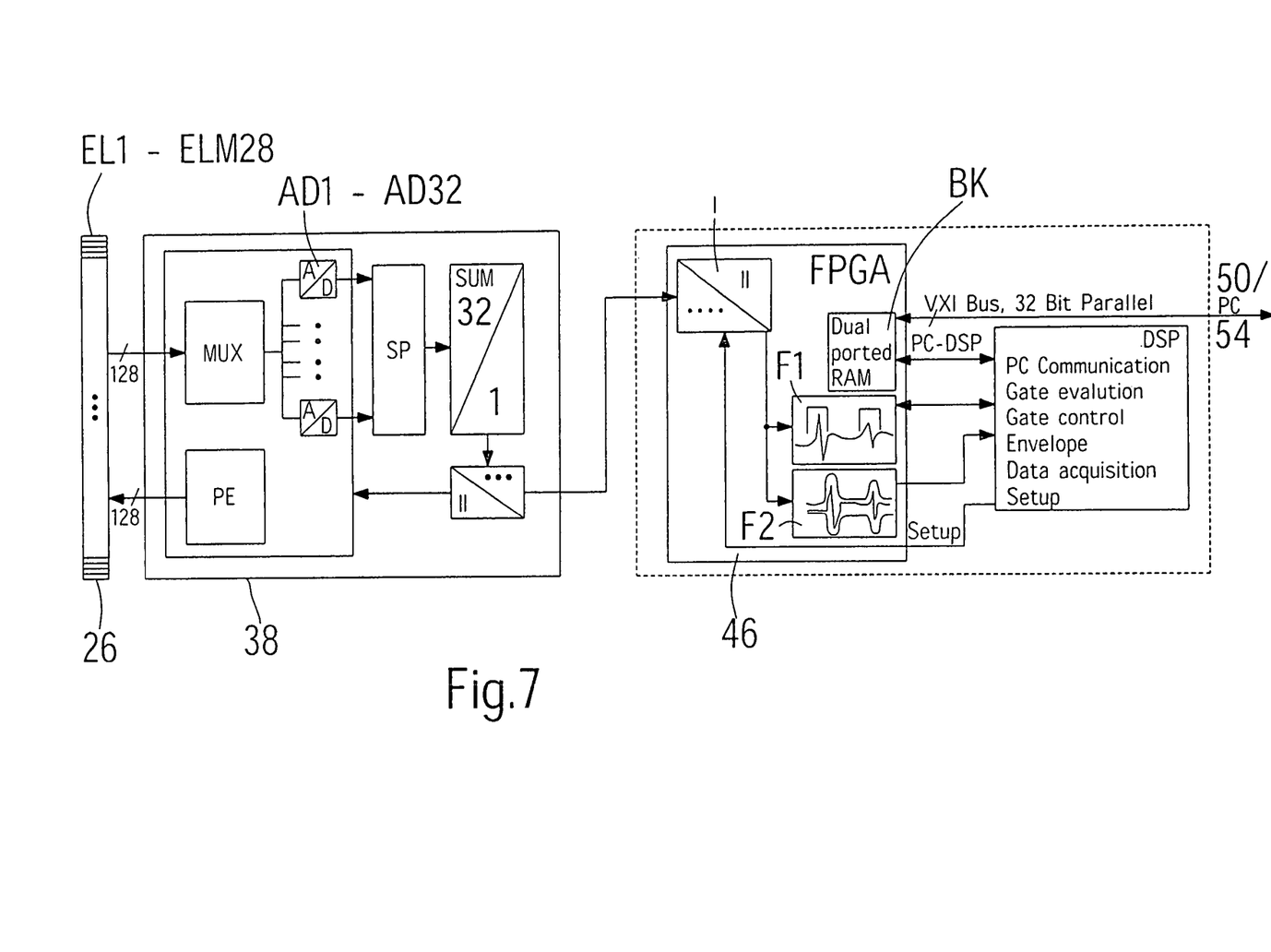
FIG. 7 shows a schematic block diagram of a circuit arrangement for processing the received signals.

FIG. 7 shows a detailed block diagram of the components of the circuit arrangement 22 according to FIG. 6. The signal processing unit 38 comprises a pulse unit PE for controlling the transmitter/receiver elements EL1-EL128, which comprise 128 elements in the present example. The transmitter elements are thereby controlled according to a definite time pattern (phasing). The receiver elements are subsequently switched to simultaneous reception and the received analog signals are then conducted via a multiplexer MUX to corresponding A/D converters AD, in the present example, to each of 32 A/D converters. The received analog signals are digitalized by the A/D converters AD and stored in a storage element SP as a so-called A-image or A-scan. The e.g. 32 A-scans stored in the storage element SP according to FIG. 4 are then added during their propagation time in a summing element SUM, according to the invention by a phase-locked addition of the amplitude values, to form the A-scan shown in FIG. 5 in their propagation time, whereby the advantage results that the amplitude peaks add up, as a result of which the defect location is clearly accentuated and noise signals mutually cancelled.

Figure 5:
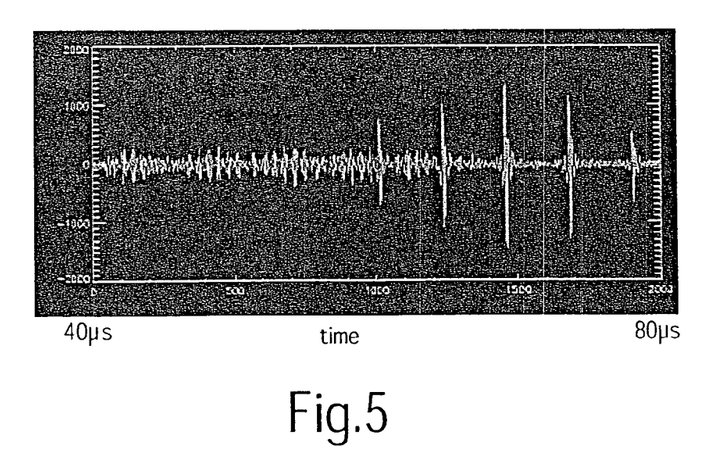
FIG. 5 shows a representation of the amplitude curve of the sums of amplitude values having the same propagation times of various receiver elements for the evaluation of a defect location.

Thus, the signal shown in FIG. 5 is available at the output of the summing element SUM as an A-scan which is forwarded via an interface I of the further signal evaluation device 46 which also has an interface I. The B-scan is then forwarded to one or more evaluation modules F1 F2 in the signal evaluation device 46 for further signal processing. The individual components of the circuit units 38, 46 are controlled via a digital signal processor DSP which is connected with the personal computer 52 and with the microprocessor unit 54 via a bus coupler BK and the interface 50. The results of the signal processing are displayed on a screen.

To obtain a data reduction prior to storing the signals applied to the A/D converters AD1-AD32, it can be provided that they be filtered, preferably wavelet filtered, prior to storing.

The method described thus far generally serves to quickly and effectively identify defect locations in an object. Since the location information of the defect location is lost during summation of the amplitude values along the same propagation times, further steps are required to enable a detection of an outer defect. For this purpose, it is proposed that the point-wave signals reflected by an outer defect of the object when examined with an ultrasonic wave be evaluated.

Figure 8:
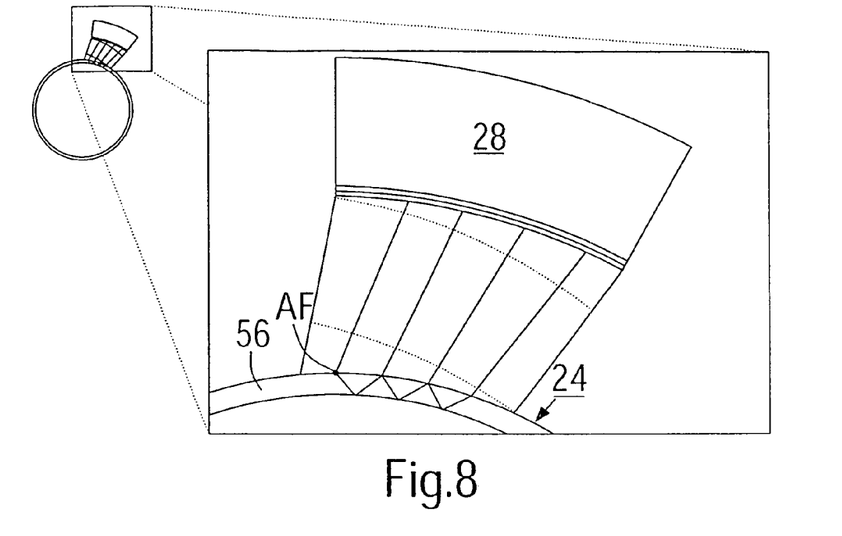
FIG. 8 shows a basic representation of the ray paths of a defect location situated on the outer surface.
Figure 9:
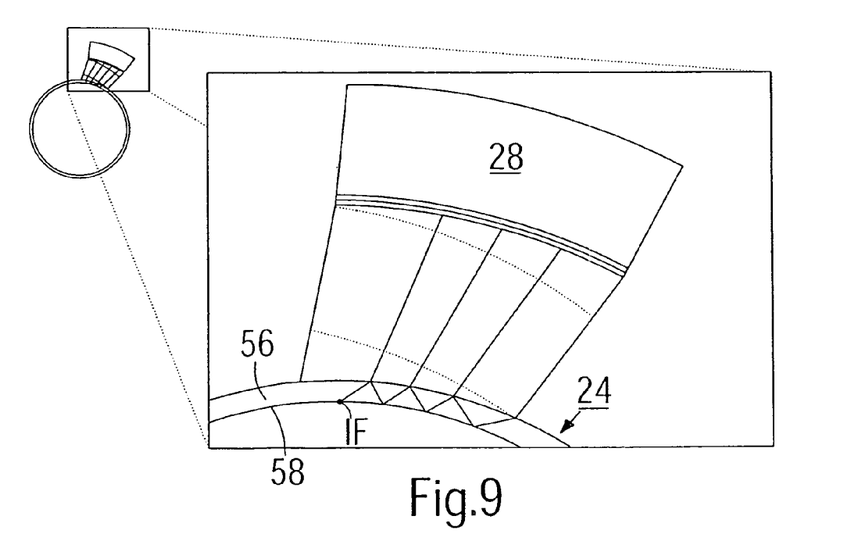
FIG. 9 shows a basic representation of the ray paths of a defect location situated on the inner surface.

FIG. 8 shows strictly schematically the ray paths when the pipe 24, which has a defect location AF in an outer surface 56, is ultrasonically irradiated. FIG. 9 shows the ray paths when the pipe 24, which has a defect location IF on an inner surface 58, is ultrasonically irradiated. The point-wave signals emanating from the outer defect AF in FIG. 8 can also be seen in the B-scan shown in FIG. 2, namely as defect echoes FE1 to FE4 and their interference pattern. To identify an outer defect, a "diagonal" addition can be performed, i.e. not during a specific propagation time but at a right angle or approximately at a right angle to the interference patterns of the received amplitude values, so that an amplitude peak is produced in this direction which contains information about an outer defect AF.

To reach a decision about whether there is an inner or outer defect, an evaluation by a coincidence method of the sum signal of the amplitude values of the same propagation times with the sum signal of the amplitude values in direction at a right angle or approximately at a right angle to the interference patterns of the amplitude values received from the point-wave signals is effected, e.g. in one of the evaluation modules F1, F2, an outer defect being present if both signals show a defect location. However, if a defect location is identified during the phase-locked addition of the amplitude values along a propagation time without, however, a defect location being detected during addition of the amplitude values at a right angle or approximately at a right angle to the interference patterns, then there is an inner defect.

The following should be noted as special advantages of the method according to the invention: the signals obtained for evaluating the defect locations exhibit a better signal/noise ratio in comparison to the prior art and can thus be evaluated better automatically. As a result of the planar ultrasonic irradiation of the object to be examined on the basis of the use of a probe with Phased Array Technology, i.e. by simultaneous transmission of a wave front and simultaneous reading of the signals, a considerable time advantage is obtained in comparison to methods with sequential technology known from the prior art.

A data reduction also takes place by the phase-locked addition, so that the subsequent signal processing is also accelerated and simplified.

Figure 10:
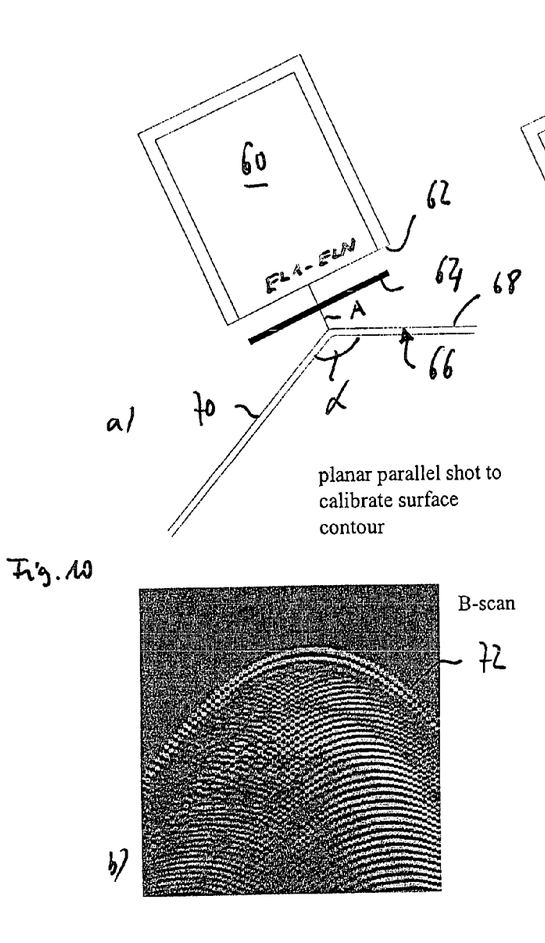
FIG. 10a shows a schematic representation of a wave front emanating from a probe for determining the contour of an object to be examined.
FIG. 10b shows a schematic representation of a received interference pattern (B-scan) of the contour of the object to be examined.

FIG. 10a shows a schematic representation of a probe 60 which corresponds in its structure to the probe 14 described above. A wave front 64 extending parallel or essentially parallel to a plane 62 fixed by the transmitter elements is emitted by the probe 60. The wave front 64 hits an object 66 having a contour, e.g. an edge, bend or curvature, which, in the present example, has a first surface 68 which extends at an angle α relative to a second surface 70.

To determine the contour of the object 60 to be examined, the waves reflected by the surfaces 68, 70 are received, digitalized and stored in a storage element SP corresponding to the circuit arrangement of FIG. 7. The contour of the object 66 can then be computed on the basis of a defined distance A from a reference point of the object 66 and the determined and stored propagation times of the signals. A corresponding interference pattern (B-scan) 72, which essentially corresponds to the contour of the object 66, is shown in FIG. 10b.

Figure 11:
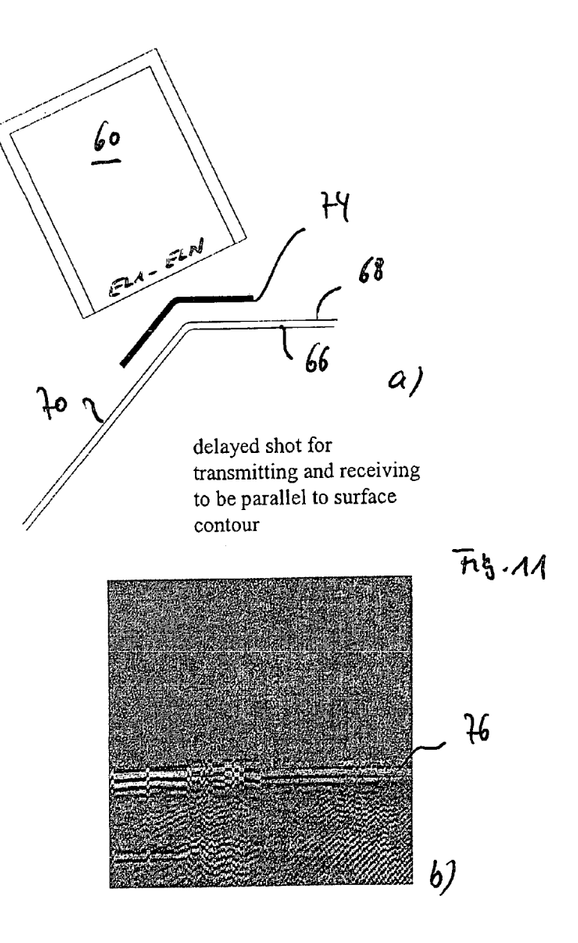
FIG. 11a shows a schematic representation of a wave front emanating from a probe which extends parallel or essentially parallel to the surface of the contour of the object to be examined.
FIG. 11b shows a schematic representation of an essentially planar interference pattern for the simple evaluation of defect locations.

Based on the computed contour of the object 66, the transmitter elements EL1-ELN are then controlled during the actual measuring process in a time-delayed manner in such a way that a wave front 74 emanating from the probe 60 extends parallel or essentially parallel to the contour, i.e. the surfaces 68, 70 of the object 60 to be examined. The waves reflected by the object 66 are also received in a time-displaced manner and from the signals thus received an interference pattern 76, shown in FIG. 11b, is generated, the wave front of the interference pattern lying in a plane.

Defect locations can be easily identified from the data of this interference pattern.

To enable an adaptation to a changing contour of the object, it is provided that the received interference pattern 76 be compared with a desired pattern and that, when the received interference pattern 76 deviates from the desired pattern, a renewed determination of the actual contour of the object 66 takes place by e.g. a planar wave front 64 being sent onto the object 66 proceeding from the probe 60, even during a measuring process, to undertake a renewed contour measurement, on which the further measurement is then based.

The invention claimed is:

1. A method for processing signals which are generated during the non-destructive examination of objects by reflection of ultrasonic waves at defect locations of the structure of the object, comprising the steps of:
   emitting a complete wave front onto at least one section of the object to be examined by means of a plurality of independent transmitter elements;
   receiving a wave reflected by the structure of the object by means of a plurality of receiver elements which are independent of one another;
   the plurality of transmitter and receiver elements constituting a probe;
   digitalizing the signals received from the receiver elements;
   storing the digitalized signals according to amplitude and propagation time in a storage element; and
   detecting defect locations by a phase-locked addition of the stored amplitude values along a propagation time.

2. The method according to claim 1, wherein a defect location on an outer surface of the object facing the probe is identified by evaluating point-wave signals passing from the defect location.

3. The method according to claim 1, wherein detection of a defect location on an outer surface of the object facing the probe is effected by an addition of amplitude values stored in the storage module which are derived from the point-wave signals proceeding from the outer defect.

4. The method according to claim 1, wherein the addition extends at a substantially right angle to an interference pattern of the received amplitude values of the point waves of defects on an outer surface of the object.

5. The method according to claim 1, wherein detection of a defect location on an outer surface of the object facing the probe is effected by a comparison of the sum signal determined during the phase-locked addition of the stored amplitude values along a propagation time with the sum signal determined during the addition of the amplitude values of an interference pattern, an outer defect being present if both sum signals indicate a defect location (coincidence method).

6. The method according to claim 1, wherein the individual transmitter elements are controlled in a time-delayed manner (phasing) to set a beam angle α adapted to test conditions.

7. The method according to claim 1, wherein a propagation time dependent amplitude correction of the sum signal determined during the addition is performed to identify the location of the defect.

8. The method according to claim 1, wherein the received signals are filtered after their digitalization for the data reduction.

9. The method according to claim 1, wherein contour of a surface of the object to be examined is recorded and stored, and the independent transmitter elements are controlled in a time-delayed manner in such a way that the emanating wave front extends substantially parallel or to the contour of the surface of the object and the waves reflected by the object are received in a time-delayed manner and generate an essentially planar interference pattern.

10. A method for the non-destructive examination of a contour of an object by processing signal waves which are generated by reflection of ultrasonic waves at defect locations of the structure of the object, comprising the steps of:
    emitting a complete wave front onto the at least one contour of the object to be examined by means of a plurality of independent transmitter elements;
    receiving a wave reflected by the structure of the object by means of a plurality of receiver elements. which are independent of one another;
    digitalizing the signals received from the receiver elements;
    storing the digitalized signals according to amplitude and propagation time in a storage element;
    recording and storing the contour of a surface of the object to be examined; and
    controlling the independent transmitter elements are controlled in a time-delayed manner such that the emanating wave front extends substantially parallel to the contour of the surface of the object and waves reflected by the object are received in a time-delayed manner and generate a substantially planar interference pattern.

11. The method according to claim 10, wherein the contour of the object is determined by emitting a planar wave front onto the contour to be examined, the waves reflected by the contour of the object are received, digitalized by means of the plurality of receiver elements which are independent of one another and the digitalized signals are stored in the storage element at least according to propagation time, and wherein the contour of the object is computed from a defined distance of the probe to the object and the different propagation times of the received signals.

12. The method according to claim 10, wherein an interference pattern determined from the received signals is compared with a desired pattern and when there is a deviation from the desired pattern, a renewed contour measurement is performed.

13. The method according to claim 10, wherein a subsequent determination of the contour of the object to be examined occurs during a measuring process.

14. The method according to claim 10, wherein the wave front extending substantially parallel to the contour of the object to be examined is generated by a time-delayed emission of sound pulses.

15. The method according to claim 10, wherein the received planar interference pattern is received by time-delayed actuation of the receiver elements which are independent of one another in dependence on the contour values stored in the storage unit.

16. A circuit arrangement for processing signals which are generated during non-destructive examination of objects by reflection of ultrasonic waves at defect locations of the structure of the object, comprising:
    a signal recording unit with a pulse generator for actuating transmitter/receiver elements for emitting a complete wave front and for switching the transmitter/receiver elements to receive, the transmitter/receiver elements constituting a probe;
    a multiplexer via which analog signals applied to the receiver elements can be transmitted to A/D converters, and
    a storage element to which outputs of converters are connected for storing digitalized signals,
    wherein the storage element includes means for storing the digitalized signals with respect to their signal amplitude and propagation time and
    a summing element for the phase-locked addition of the amplitude values stored in the storage element is arranged in tandem behind the storage element and a signal which can be evaluated with respect to the defect location is applied to an output of the summing element.

17. The circuit arrangement according to claim 16, wherein the output of the summing element is connected via an interface I with an evaluation circuit in which an output of the summing element is connected with a signal processing circuit which has one or more evaluation modules for further assessment and evaluation of the signal applied to the output of the summing element.

18. The circuit arrangement according to claim 16, wherein the evaluation module has a coincidence circuit for comparing the sum signals during a phase-locked addition of the amplitude values along a propagation time with the sum signals during addition of the amplitude values of the point-wave signals of outer defects.

19. The circuit arrangement according to claim 16, wherein the probe is configured as a Phased Array Transducer.

20. The circuit arrangement according to claim 16, wherein the transmitter/receiver elements are constructed and arranged to be controlled simultaneously or in a phase-shifted manner (phasing).

21. The circuit arrangement according to claim 16, wherein the transmitter/receiver elements are made as a unit.

22. The circuit arrangement according to claim 16, wherein the transmitter elements and receiver elements are made as separate units.

* * * * *